United States Patent
Pittam et al.

(10) Patent No.: US 8,063,210 B2
(45) Date of Patent: Nov. 22, 2011

(54) PROCESS AND INTERMEDIATE

(75) Inventors: John David Pittam, Cheshire (GB); George Joseph Sependa, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 1177 days.

(21) Appl. No.: 11/748,655

(22) Filed: May 15, 2007

(65) Prior Publication Data

US 2007/0270384 A1 Nov. 22, 2007

(30) Foreign Application Priority Data

May 16, 2006 (GB) .................................. 0609617.6

(51) Int. Cl.
*C07F 9/02* (2006.01)
(52) U.S. Cl. ...................................... 544/244; 544/284
(58) Field of Classification Search .................. 514/109, 514/266.2; 544/244, 284
See application file for complete search history.

(56) References Cited

FOREIGN PATENT DOCUMENTS

| WO | 2004/058752 A1 | 7/2004 |
|---|---|---|
| WO | 2004/058781 A1 | 7/2004 |
| WO | WO 2004058781 A1 * | 7/2004 |
| WO | 2004/094410 A1 | 11/2004 |
| WO | 2004/105764 A1 | 12/2004 |

OTHER PUBLICATIONS

Jung et al, "Discovery of Novel and potent Thiazoloquinazolines as selective Aurora A and B Kinase Inhibitors", J Med Chem, Jan. 10, 2006, pp. 955-970, vol. 49.

* cited by examiner

*Primary Examiner* — James O Wilson
*Assistant Examiner* — Alexander R Pagano

(57) ABSTRACT

The invention relates to a new process useful in the preparation of pharmaceutical compounds such as 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate (AZD1152) and intermediates used therein.

6 Claims, No Drawings

PROCESS AND INTERMEDIATE

This application claims the benefit under 35 U.S.C. §119 (a)-(d) of Application No. 0609617.6 (GB) filed on May 16, 2006.

The invention relates to a new process useful in the preparation of pharmaceutical compounds such as 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate (herein referred to as AZD1152), which is an aurora kinase inhibitor that is useful in the treatment of hyperproliferative diseases such as cancer. In particular the invention relates to a process for the preparation of the phosphate prodrug forms of certain aurora kinase inhibitors. The invention also relates to novel intermediates for use in said process.

Cancer (and other hyperproliferative diseases) is characterised by uncontrolled cellular proliferation which occurs when normal regulation of cell proliferation is lost. This loss often appears to be the result of genetic damage to the cellular pathways that control a cell's progress through its cell cycle.

In eukaryotes, an ordered cascade of protein phosphorylation is thought to control the cell cycle. Several families of protein kinases that play critical roles in this cascade have been identified. The activity of many of these kinases is increased in human tumours when compared to normal tissue. This can occur by either increased levels of expression of the protein (for example as a result of gene amplification), or by changes in expression of co activators or inhibitory proteins.

The first identified, and most widely studied of these cell cycle regulators are the cyclin dependent kinases (or CDKs). More recently, protein kinases that are structurally distinct from the CDK family have been identified and found to play critical roles in regulating the cell cycle. These kinases also appear to be important in oncogenesis and include human homologues of the *Drosophila* aurora and *S. cerevisiae* Ipl1 proteins. The three human homologues of these genes aurora-A, aurora-B and aurora-C (also known as aurora2, aurora1 and aurora3 respectively) encode cell cycle regulated serine-threonine protein kinases (summarised in Adams et al., 2001, Trends in Cell Biology. 11(2): 49-54). These show a peak of expression and kinase activity through G2 and mitosis. Several observations implicate the involvement of human aurora proteins in cancer. The aurora-A gene maps to chromosome 20q13, a region that is frequently amplified in human tumours including both breast and colon tumours. Aurora-A may be the major target gene of this amplicon, since aurora-A DNA is amplified and mRNA overexpressed in greater than 50% of primary human colorectal cancers. In these tumours aurora-A protein levels appear greatly elevated compared to adjacent normal tissue. In addition, transfection of rodent fibroblasts with human aurora-A leads to transformation, conferring the ability to grow in soft agar and form tumours in nude mice (Bischoff et al., 1998, The EMBO Journal. 17(11): 3052-3065). Other work (Zhou et al., 1998, Nature Genetics. 20(2): 189-93) has shown that artificial overexpression of aurora-A leads to an increase in centrosome number and an increase in aneuploidy, a known event in the development of cancer.

It has also been shown that there is an increase in expression of aurora-B (Adams et al., 2001, Chromsoma. 110(2): 65-74) and aurora-C (Kimura et al., 1999, Journal of Biological Chemistry, 274(11): 7334-40) in tumour cells when compared to normal cells. Aurora-B is overexpressed in cancer cells and increased levels of aurora-B have been shown to correlate with advanced stages of colorectal cancer (Katayama et al. (1999) J. Natl. Cancer Inst. 91:1160). Furthermore, one report suggests that overexpression of aurora-B induces aneuploidy through increased phosphorylation of histone H3 at serine 10 and that cells overexpressing aurora-B form more aggressive tumours that develop metastases (Ota, T. et al., 2002, Cancer Res. 62: 5168-5177). Aurora-B is a chromosome passenger protein which exists in a stable complex with at least three other passenger proteins, Survivin, INCENP and Borealin (Carmena M. et al. 2003, Nat. Rev. Mol. Cell. Biol. 4: 842-854). Survivin is also upregulated in cancer and contains a BIR (Baculovirus Inhibitor of apoptosis protein (IAP) Repeat) domain and may therefore play a role in protecting tumour cells from apoptosis and/or mitotic catastrophe.

With regard to aurora-C, its expression is thought to be restricted to the testis but it has been found to be overexpressed in various cancer lines. (Katayama H et al., 2003, Cancer and Metastasis Reviews 22: 451-464).

Importantly, it has also been demonstrated that abrogation of aurora-A expression and function by antisense oligonucleotide treatment of human tumour cell lines (WO 97/22702 and WO 99/37788) leads to cell cycle arrest and exerts an antiproliferative effect in these tumour cell lines. Additionally, small molecule inhibitors of aurora-A and aurora-B have been demonstrated to have an antiproliferative effect in human tumour cells (Keen et al. 2001, Poster #2455, American Association of Cancer Research annual meeting), as has selective abrogation of aurora-B expression alone by siRNA treatment (Ditchfield et al. 2003, journal of Cell Biology, 161(2): 267-280). This indicates that inhibition of the function of aurora-A and/or aurora-B will have an antiproliferative effect that may be useful in the treatment of human tumours and other hyperproliferative disease. The inhibition of aurora kinases as a therapeutic approach to these diseases may have significant advantages over targeting signalling pathways upstream of the cell cycle (e.g. those activated by growth factor receptor tyrosine kinases such as epidermal growth factor receptor (EGFR) or other receptors). Since the cell cycle is ultimately downstream of all of these diverse signalling events, cell cycle directed therapies such as inhibition of aurora kinases would be predicted to be active across all proliferating tumour cells, whilst approaches directed at specific signalling molecules (e.g. EGFR) would be predicted to be active only in the subset of tumour cells which express those receptors. It is also believed that significant "cross talk" exists between these signalling pathways meaning that inhibition of one component may be compensated for by another.

Inhibitors of the aurora kinases are described in International Patent Applications WO 03/55491 and WO 2004/058781, and in particular WO 2004/058781 discloses a compound which possesses the following structural formula (IA), referred to herein as AZD1152:

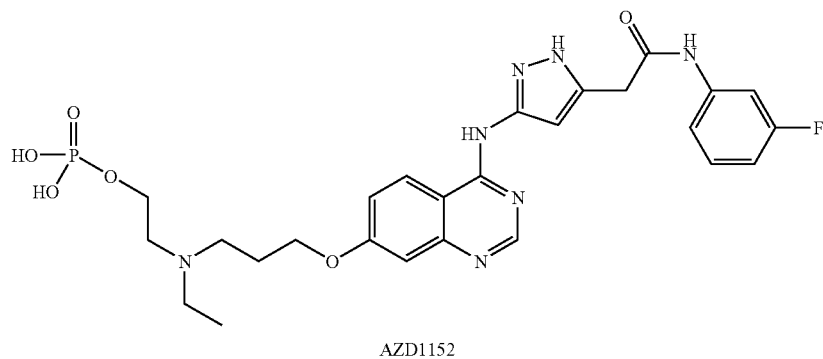

AZD1152

AZD1152 is a pro-drug that is rapidly and completely converted (in human plasma) to the active moiety which possesses the following structural formula (IVA) referred to herein as AZD1152 HQPA:

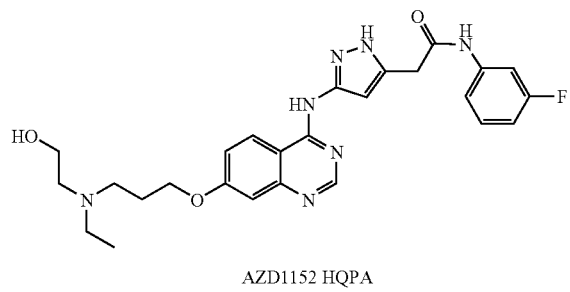

AZD1152 HQPA

AZD1152 HQPA is an ATP-competitive and reversible inhibitor of the aurora kinases with potent activity against aurora A, B-INCENP and C-INCENP (Ki's 1369±419.2 nM, 0.359±0.386 nM and 17.03±12.2 nM respectively). AZD1152 has been found to inhibit tumour growth in a panel of human colorectal (SW620, HCT116, Colo205) and lung (A549, Calu-6) tumour xenografts with statistical significance.

WO 2004/058781 discloses a general process route for the preparation of compounds of a similar to type to AZD1152. WO 2004/058781 also disclosed a process route for the preparation of AZD1152. A summary of this process is shown in scheme 1.

The present invention relates to an improved process for the preparation of AZD1152 and similar compounds. In particular, the invention relates to an improved process for the preparation of AZD1152 from AZD1152 HQPA. An outline of this process as it relates specifically to AZD1152 is shown in scheme 2. This process differs from the previously disclosed process in that it includes a novel intermediate of formula (IIA):

formula (IIA)

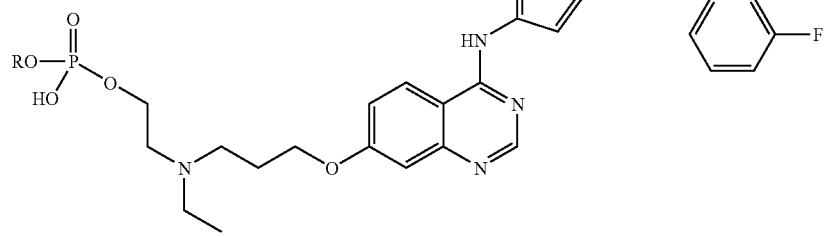

We have discovered that this intermediate can be easily isolated and is surprisingly easier to isolate than the previously disclosed intermediate of formula (IIIA)

formula (IIIA)

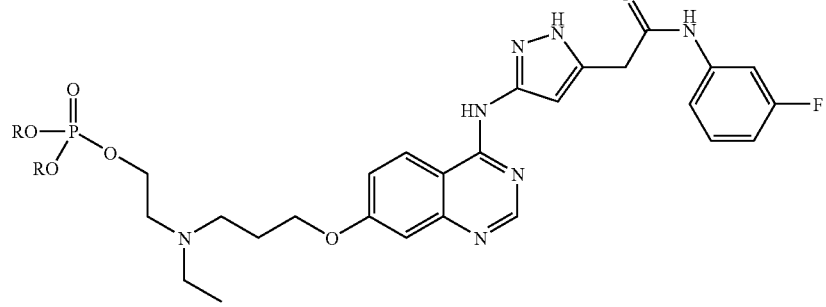

Consequently the process of the invention allows for the preparation of compounds such as AZD1152 with fewer impurities and improved yields.

Accordingly, the present invention provides a process for preparing an intermediate compound of formula (II)

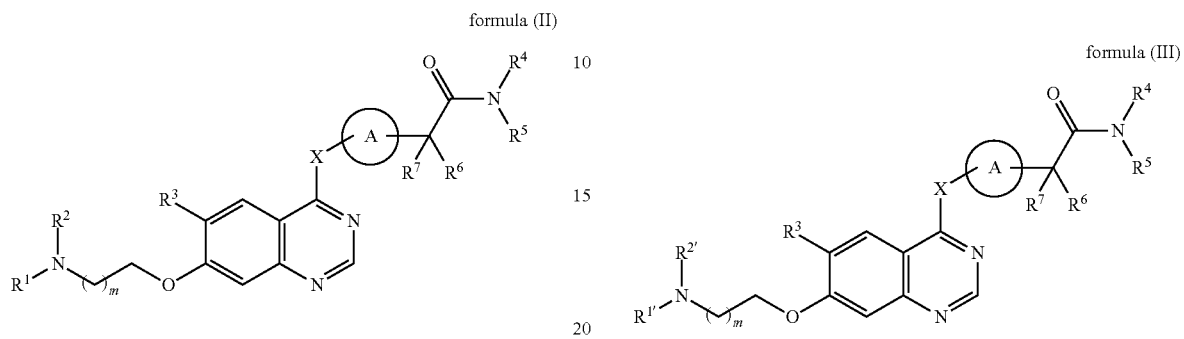

formula (II)

wherein A is 5-membered heteroaryl containing a nitrogen atom and optionally containing 1, 2 or 3 further nitrogen atoms;

X is —NH— or —N($C_{1-4}$alkyl)-;

m is 0, 1, 2 or 3;

$R^1$ is $C_{1-6}$alkyl substituted by —OP(O)(OH)(OR) and optionally further substituted by 1 or 2 $C_{1-4}$alkoxy groups;

$R^2$ is hydrogen or $C_{1-6}$alkyl optionally substituted by 1, 2 or 3 $C_{1-4}$alkoxy groups or —S(O)$_p$$R^5$ (where p is 0, 1 or 2), or $R^2$ is a group selected from $C_{2-6}$alkenyl, $C_{2-6}$alkynyl, $C_{3-6}$cycloalkyl and $C_{3-6}$cycloalkyl$C_{1-4}$alkyl;

or $R^1$ and $R^2$ together with the nitrogen to which they are attached form a 5- to 7-membered ring which ring may be saturated, unsaturated or partially saturated, wherein the ring is substituted by a group selected from —OP(O)(OH)(OR) and $C_{1-4}$alkyl which $C_{1-4}$alkyl is substituted by —OP(O)(OH)(OR), and where the ring is optionally further substituted by 1, 2 or 3 $C_{1-4}$alkyl groups;

$R^3$ is a group selected from hydrogen, halo, cyano, nitro, $C_{1-6}$alkoxy, $C_{1-6}$alkyl;

$R^4$ is hydrogen or a group selected from $C_{1-4}$alkyl, heteroaryl, heteroaryl$C_{1-4}$alkyl, aryl and aryl$C_{1-4}$alkyl which group is optionally substituted by 1, 2 or 3 substitutents selected from methyl, ethyl, cyclopropyl and ethynyl;

$R^5$ is selected from hydrogen, $C_{1-4}$alkyl, $C_{2-4}$alkenyl, $C_{2-4}$alkynyl, $C_{3-6}$cycloalkyl and $C_{3-6}$cycloalkyl$C_{1-4}$alkyl;

$R^6$ and $R^7$ are independently selected from hydrogen, $C_{1-4}$alkyl, $C_{3-6}$cycloalkyl and $C_{1-4}$alkoxy;

$R^8$ is hydrogen or $C_{1-4}$alkyl;

wherein R is an acid liable protecting group such as tert-butyl, trityl, p-methoxyphenyl, benzyl or phenyl;

which process comprises adjusting the pH of a solution of a compound of formula (III)

formula (III)

wherein A, X, m, $R^3$, $R^4$, $R^5$, $R^6$ and $R^7$ are as defined for formula (II);

$R^{1'}$ is $C_{1-6}$alkyl substituted by —OP(O)(OR)$_2$ and optionally further substituted by 1 or 2 $C_{1-4}$alkoxy groups;

$R^{2'}$ is hydrogen or $C_{1-6}$alkyl optionally substituted by 1, 2 or 3 $C_{1-4}$alkoxy groups or —S(O)$_p$$R^5$ (where p is 0, 1 or 2), or $R^{2'}$ is a group selected from $C_{2-6}$alkenyl, $C_{2-6}$alkynyl, $C_{3-6}$cycloalkyl and $C_{3-6}$cycloalkyl$C_{1-4}$alkyl;

or $R^{1'}$ and $R^{2'}$ together with the nitrogen to which they are attached form a 5- to 7-membered ring which ring may be saturated, unsaturated or partially saturated, wherein the ring is substituted by a group selected from —OP(O)(OR)$_2$ and $C_{1-4}$alkyl which $C_{1-4}$alkyl is substituted by —OP(O)(OR)$_2$, and where the ring is optionally further substituted by 1, 2 or 3 $C_{1-4}$alkyl groups;

$R^8$ is hydrogen or $C_{1-4}$alkyl;

to pH 5 to 6.5 at a temperature of −10° C. to 40° C.

Suitably R is tert-butyl.

Suitably the pH is adjusted to a pH in the range pH 5 to 6.5 at temperature of between 10° C. and 25° C. More suitably, the pH is adjusted to a pH in the range pH 5 to 6.5 at ambient temperature, such as approximately 20° C.

Suitable solvents with which to form a solution of a compound of formula (III) include, in general, dipolar aprotic liquids such as dimethylacetamide (DMA) and N-methylpyrrolidone (NMP) or mixtures thereof. The solvents may contain water in various proportions.

One embodiment of this aspect of the invention provides a process for preparing an intermediate compound of formula (IIA)

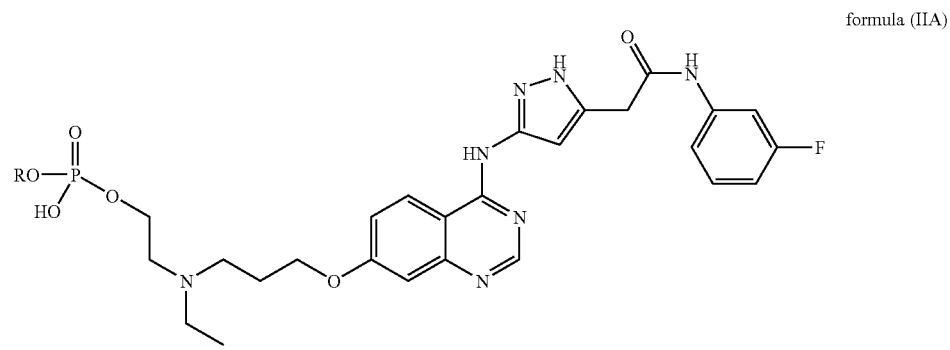

formula (IIA)

wherein R is an acid liable protecting group such as tert-butyl, trityl, p-methoxyphenyl, benzyl or phenyl;
which process comprises adjusting the pH of a solution of a compound of formula (IIIA)

ring is substituted by a group selected from —OP(O)(OH)$_2$ and C$_{1-4}$alkyl which C$_{1-4}$alkyl is substituted by —OP(O)(OH)$_2$, and where the ring is optionally further substituted by 1, 2 or 3 C$_{1-4}$alkyl groups;

formula (IIIA)

wherein R is as defined in relation to formula (IIA);
to pH 5 to 6.5 at a temperature of −10° C. to ambient temperature.

Suitably R is tert-butyl.

Suitably the pH is adjusted to a pH in the range pH 5 to 6.5 at temperature of between 10° C. and 25° C. More suitably, the pH is adjusted to a pH in the range pH 5 to 6.5 at ambient temperature, such as approximately 20° C.

Suitable solvents with which to form a solution of a compound of formula (IIIA) include, in general, dipolar aprotic liquids such as dimethylacetamide (DMA) and N-methylpyrrolidone (NMP) or mixtures thereof. The solvents may contain water in various proportions.

The invention also provides a process for the preparation of a compound of formula (I) or a pharmaceutically acceptable salt thereof:

formula (I)

wherein A is 5-membered heteroaryl containing a nitrogen atom and optionally containing 1, 2 or 3 further nitrogen atoms;
X is —NH— or —N(C$_{1-4}$alkyl)-;
m is 0, 1, 2 or 3;
R$^1$ is C$_{1-6}$alkyl substituted by —OP(O)(OH)$_2$ and optionally further substituted by 1 or 2 C$_{1-4}$alkoxy groups;
R$^2$ is hydrogen or C$_{1-6}$alkyl optionally substituted by 1, 2 or 3 C$_{1-4}$alkoxy groups or —S(O)$_p$R$^8$ (where p is 0, 1 or 2), or R$^2$ is a group selected from C$_{2-6}$alkenyl, C$_{2-6}$alkynyl, C$_{3-6}$cycloalkyl and C$_{3-6}$cycloalkylC$_{1-4}$alkyl;
or R$^1$ and R$^2$ together with the nitrogen to which they are attached form a 5- to 7-membered ring which ring may be saturated, unsaturated or partially saturated, wherein the R$^3$ is a group selected from hydrogen, halo, cyano, nitro, C$_{1-6}$alkoxy, C$_{1-6}$alkyl;
R$^4$ is hydrogen or a group selected from C$_{1-4}$alkyl, heteroaryl, heteroarylC$_{1-4}$alkyl, aryl and arylC$_{1-4}$alkyl which group is optionally substituted by 1, 2 or 3 substitutents selected from methyl, ethyl, cyclopropyl and ethynyl;
R$^5$ is selected from hydrogen, C$_{1-4}$alkyl, C$_{2-4}$alkenyl, C$_{2-4}$alkynyl, C$_{3-6}$cycloalkyl and C$_{3-6}$cycloalkylC$_{1-4}$alkyl;
R$^6$ and R$^7$ are independently selected from hydrogen, C$_{1-4}$alkyl, C$_{3-6}$cycloalkyl and C$_{1-4}$alkoxy;
R$^8$ is hydrogen or C$_{1-4}$alkyl;
from a compound of formula (II) as described herein which process comprises the steps of:

1) adding a suitable acid to a solution of a compound of formula (II) as defined herein;
2) adjusting the pH to within the range pH 4.5 to 5.5; and thereafter if necessary or desired
3) converting the compound of formula (I) into a pharmaceutically acceptable salt thereof.

Suitable solvents with which to form a solution of a compound of formula (II) include dipolar aprotic liquids such as dimethylacetamide (DMA) and N-methylpyrrolidone (NMP) or mixtures thereof. The solvents may contain water in various proportions.

Suitably, the acid used in step 1) is selected from hydrochloric acid, fumaric acid, trifluoroacetic acid, ethanedisulphonic acid, methanesulphonic acid, sodium bisulphate or any other cid with a pKa sufficient to facilitate removal of the acid labile protecting group.

Suitably, in step 2), the pH is adjusted to within the range pH 4.5 to 5.5 by the addition of an appropriate base. Such a base may be selected from a hydroxide of an alkali metal such as sodium, potassium or lithium.

Suitably, step 2) is carried out at a temperature at which the reaction mixture remains a solution such as between 15° C. and 60° C.

An appropriate solvent for step 2) may be a mixture of tetrahydrofuran (THF) and water, preferably in equal volumes.

One embodiment of this aspect of the invention provides a process for the preparation of AZD 1152 (formula (IA))

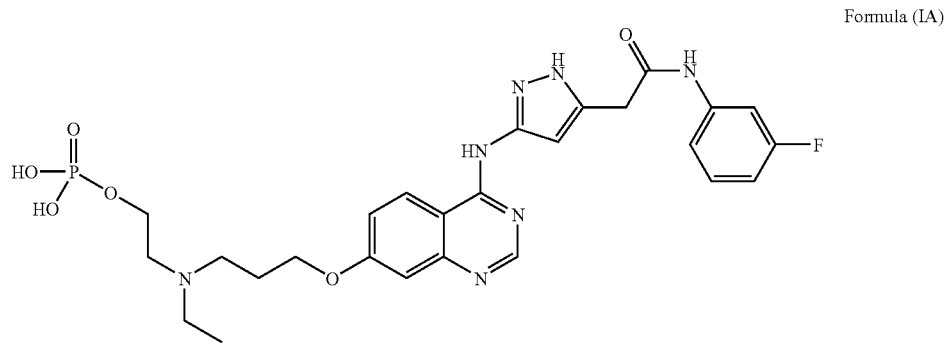

Formula (IA)

from a compound of formula (IIA)

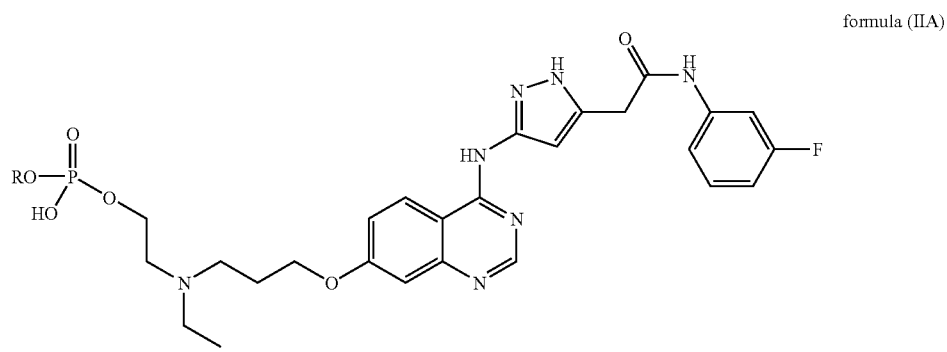

formula (IIA)

wherein R is tert-butyl;
which process comprises the steps of:
1) adding a suitable acid to a solution of a compound of formula (IIA); and
2) adjusting the pH of the resulting mixture to pH 4.5 to 5.5; and then optionally
3) forming a pharmaceutically acceptable salt of AZD 1152.

Suitable solvents with which to form a solution of a compound of formula (IIA) include dipolar aprotic liquids such as dimethylacetamide (DMA) and N-methylpyrrolidone (NMP) or mixtures thereof. The solvents may contain water in various proportions.

Suitably, the acid used in step 1) is selected from hydrochloric acid, fumaric acid, trifluoroacetic acid, ethanedisulphonic acid, methanesulphonic acid, sodium bisulphate or any other acid with a pKa sufficient to facilitate removal of the acid labile protecting group.

Suitably, in step 2), the pH is adjusted to within the range pH 4.5 to 5.5 by the addition of an appropriate base. Such a base may be selected from a hydroxide of an alkali metal such as sodium, potassium or lithium.

Suitably, step 2) is carried out at a temperature at which the reaction mixture remains a solution such as between 15° C. and 60° C., and particularly at room temperature.

An appropriate solvent for step 2) may be a mixture of tetrahydrofuran (THF) and water, preferably in equal volumes.

The compound of formula (II) is a novel intermediate and forms a further feature of the invention. The compound of formula (IIA) is also a novel intermediate and forms yet another feature of the invention A further aspect of the invention provides a process for the preparation of AZD1152 (formula (IA))

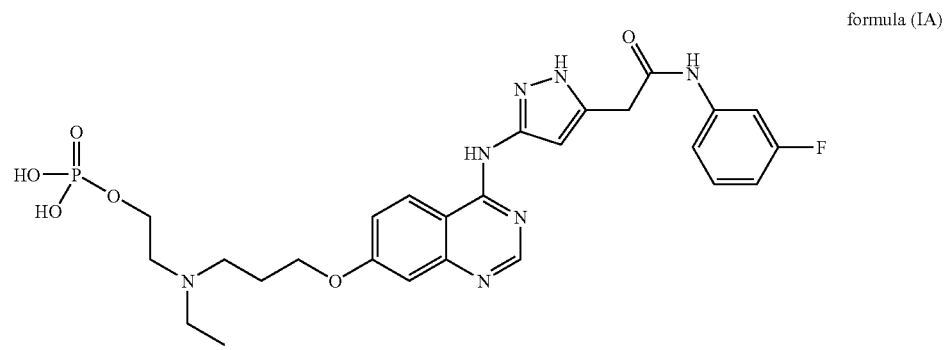

formula (IA)

from a compound of formula (IIIA)

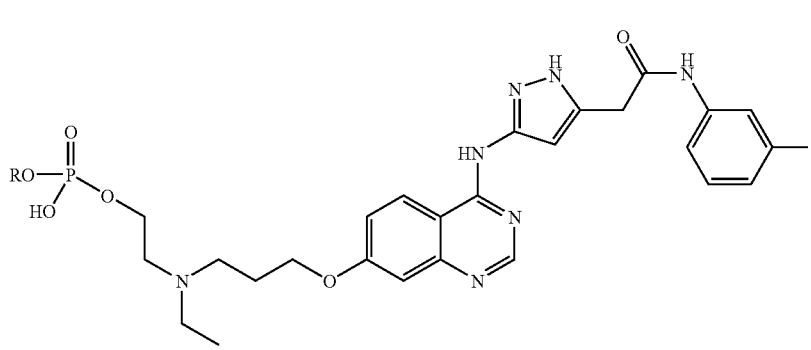

formula (IIIA)

wherein the process comprises the steps of:
(i) adjusting the pH of a solution of a compound of formula (IIIA), wherein R is as defined in relation to formula (IIA) above, to pH 5 to 6.5 at a temperature of −10° C. to ambient temperature to form a compound of Formula (IIA):

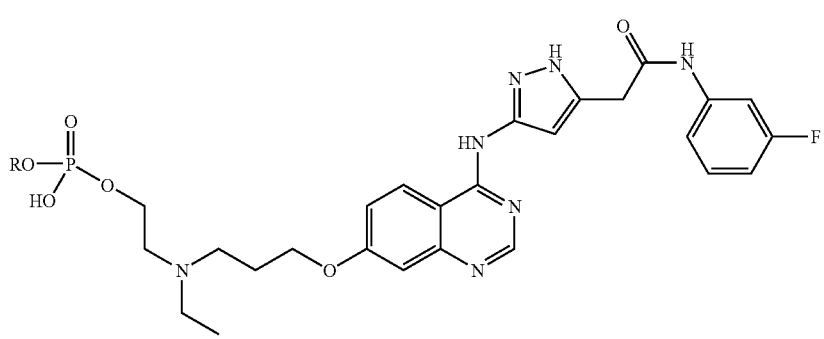

formula (IIA)

(ii) adding a suitable acid to a solution of a compound of formula (IIA);
(iii) adjusting the pH of the resulting mixture to pH 4.5 to 5.5 to form AZD1152 (formula (IA));
and then optionally forming a pharmaceutically acceptable salt of AZD1152.

For step (i) above:
Suitably R is tert-butyl.
Suitably the pH is adjusted to a pH in the range pH 5 to 6.5 at temperature of between 10° C. and 25° C. More suitably, the pH is adjusted to a pH in the range pH 5 to 6.5 at ambient temperature, such as approximately 20° C.
Suitable solvents with which to form a solution of a compound of formula (IIIA) include, in general, dipolar aprotic liquids such as dimethylacetamide (DMA) and N-methylpyrrolidone (NMP) or mixtures thereof. The solvents may contain water in various proportions.

For step (ii) above:
Suitable solvents with which to form a solution of a compound of formula (II) include dipolar aprotic liquids such as dimethylacetamide (DMA) and N-methylpyrrolidone (NMP) or mixtures thereof. The solvents may contain water in various proportions. Suitably, the acid used in step (ii) is selected from hydrochloric acid, fumaric acid, trifluoroacetic acid, ethanedisulphonic acid, methanesulphonic acid, sodium bisulphate or any other acid with a pKa sufficient to facilitate removal of the acid labile protecting group.

For step (iii) above:
The pH is adjusted to within the range pH 4.5 to 5.5 by the addition of an appropriate base. Such a base may be selected from a hydroxide of an alkali metal such as sodium, potassium or lithium.

Suitably, step (iii) is carried out at a temperature at which the reaction mixture remains a solution such as between 15° C. and 60° C., and particularly at room temperature.
An appropriate solvent for step (iii) may be a mixture of tetrahydrofuran (THF) and water, preferably in equal volumes.

Within the present invention, it is to be understood that, insofar as certain compounds described herein defined may exist in optically active or racemic forms by virtue of one or more asymmetric carbon atoms, the invention includes in its definition any such optically active or racemic form. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques.

Within the present invention it is to be understood that a compound described herein may exhibit the phenomenon of tautomerism and that the formulae drawings within this specification can represent only one of the possible tautomeric forms. It is to be understood that the invention encompasses any tautomeric forms and is not to be limited merely to any one tautomeric form utilised within the formulae drawings.

It is also to be understood that certain compounds described herein may exist in solvated as well as unsolvated forms such as, for example, hydrated forms. It is to be understood that the invention encompasses all such solvated forms.

The present invention relates to the compounds of formula (I) as herein defined as well as to the salts thereof. Salts for use in pharmaceutical compositions will be pharmaceutically acceptable salts, but other salts may be useful in the production of the compounds of formula (I) and their pharmaceutically acceptable salts. Pharmaceutically acceptable salts of the invention may, for example, include acid addition salts of compounds of formula (I) as herein defined which are sufficiently basic to form such salts. Such acid addition salts include but are not limited to fumarate, methanesulphonate, hydrochloride, hydrobromide, citrate, ethanedisulphonate and maleate salts and salts formed with phosphoric and sulphuric acid. In addition where compounds of formula (I) are sufficiently acidic, salts are base salts and examples include but are not limited to, an alkali metal salt for example sodium or potassium, an alkaline earth metal salt for example calcium or magnesium, or organic amine salt for example triethylamine, ethanolamine, diethanolamine, triethanolamine, morpholine, N-methylpiperidine, N-ethylpiperidine, dibenzylamine or amino acids such as lysine.

In this specification the generic term "alkyl" includes both straight-chain and branched-chain alkyl groups. However references to individual alkyl groups such as "propyl" are specific for the straight chain version only and references to individual branched-chain alkyl groups such as "tert-butyl" are specific for the branched chain version only. An analogous convention applies to other generic terms, for example "alkenyl" and "alkynyl".

"Cycloalkyl" is a monocyclic, saturated alkyl ring and "aryl" is a monocyclic or bicyclic aromatic ring.

Unless otherwise specified "heteroaryl" is a monocyclic or bicyclic aromatic ring containing 5 to 10 ring atoms of which 1, 2, 3 or 4 ring atoms are chosen from nitrogen, sulphur or oxygen where a ring nitrogen or sulphur may be oxidised.

Where optional substituents are chosen from "1 or 2" or from "1, 2, or 3" groups or substituents it is to be understood that this definition includes all substituents being chosen from one of the specified groups i.e. all substituents being the same or the substituents being chosen from two or more of the specified groups i.e. the substituents not being the same.

Compounds of the present invention have been named with the aid of computer software (ACD/Name version 6.6 or ACD Name Batch version 6.0).

Suitable values for any R group (R and $R^1$ to $R^8$) or any part or substitutent for such groups include:

| | |
|---|---|
| for $C_{1-4}$alkyl: | methyl, ethyl, propyl, isopropyl, butyl, 2-methylpropyl and tert-butyl; |
| for $C_{1-6}$alkyl: | $C_{1-4}$alkyl, pentyl, 2,2-dimethylpropyl, 3-methylbutyl and hexyl; |
| for $C_{2-4}$alkenyl: | vinyl, allyl and 1-propenyl; |
| for $C_{2-6}$alkenyl: | $C_{2-4}$alkenyl, 1-butenyl, 2-butenyl, 3-butenyl, 2-methylbut-2-enyl, 3-methylbut-1-enyl, 1-pentenyl, 3-pentenyl and 4-hexenyl; |
| for $C_{2-4}$alkynyl: | ethynyl, 1-propynyl, 2-propynyl and 3-butynyl; |
| for $C_{2-6}$alkynyl: | $C_{2-4}$alkynyl, 2-pentynyl, hexynyl and 1-methylpent-2-ynyl; |
| for $C_{3-6}$cycloalkyl: | cyclopropyl, cyclobutyl, cyclopentyl and cyclohexyl; |
| for $C_{3-6}$cycloalkyl$C_{1-4}$alkyl: | cyclopropylmethyl, cyclopropylethyl, cyclobutylmethyl, cyclopentylmethyl and cyclohexylmethyl; |
| for aryl: | phenyl and naphthyl; |
| for aryl$C_{1-4}$alkyl: | benzyl, phenethyl, naphthylmethyl and naphthylethyl; |

-continued

| | |
|---|---|
| for halo: | fluoro, chloro, bromo and iodo; |
| for $C_{1-4}$alkoxy: | methoxy, ethoxy, propoxy and isopropoxy; |
| for $C_{1-6}$alkoxy: | $C_{1-4}$alkoxy, pentyloxy, 1-ethylpropoxy and hexyloxy; |
| for heteroaryl: | pyridyl, imidazolyl, quinolinyl, cinnolyl, pyrimidinyl, thiophenyl, pyrrolyl, pyrazolyl, thiazolyl, triazolyl, oxazolyl, isoxazolyl and pyrazinyl and preferably thiazolyl, pyridyl, imidazolyl and pyrimidinyl; |
| for heteroaryl$C_{1-4}$alkyl: | pyridylmethyl, pyridylethyl, pyrimidinylethyl, pyrimidinylpropyl, pyrimidinylbutyl, imidazolylpropyl, imidazolylbutyl, quinolinylbutyl, 1,3,4-triazolylpropyl and oxazolylmethyl; |

It should be noted that examples given for terms used in the description are not limiting.

The invention is illustrated herein by means of non-limiting Examples, data and Figures in which, unless otherwise stated:—

(i) yields are given for illustration only and are not necessarily the maximum attainable;

(ii) where a product is used for seeding it can be obtained by prior known process such as those described in WO 2004/058781;

(iii) the identity of compounds prepared as described herein was generally confirmed by $^1$H NMR at 400 MHz in hexadeuterated dimethylsulphoxide with added tetramethylsilane (TMS) for reference (TMS=0.00 ppm), trifluoroacetic acid to aid solubility and an internal standard such as maleic acid.

As described herein AZD 1152 and AZD 1152 HQPA are disclosed in WO 2004/058781. The process details provided in WO2004/058781 in relation to AZD1152, AZD1152 HQPA and all the intermediates en route to said compounds are incorporated herein by reference in their entirety.

Preparation of
7-(3-hydroxypropoxy)quinazolin-4(3H)-one

2-Amino-4-fluorobenzoic acid and 1,3-propanediol were stirred together and heated to 120° C. Formamidine acetate was added and the mixture stirred for 3.5 hour to yield 7-fluoroquinazoline-4-one. A solution of potassium hydroxide in 1,3-propanediol was then added to the mixture over a period of 2 hours and 50 minutes, which was then cooled 15° C. Following this, the mixture was heated to 125° C. for 5 hour before cooling to 75° C. Dilute hydrochloric acid (about 6% w/w) was gradually added to the reaction mixture until pH 4.5 was achieved. The mixture was cooled to 0° C. over 6 hour and maintained at that temperature for a further hour prior to isolation of the crude product by centrifugation. The crude material washed with water and dried in vacuo before dissolving in methanol at gentle reflux and partially concentrating under reduced pressure at a temperature of 42° C. This solution was then cooled to 0° C. over a period of 3 hour and the resultant product was isolated by filtration, prior to drying in vacuo. 7-(3-Hydroxypropoxy)quinazolin-4(3H)-one was recovered in a 73% yield.

$^1$H-NMR (DMSO $d_6$): 11.90 (br s, 1H), 8.04 (s, 1H), 8.00 (d, 1H), 7.10 (m, 2H), 4.17 (t, 2H), 3.58 (t, 2H), 1.92 (m, 2H) MS (+ve ESI): 221 (M+H)$^+$

Preparation of
4-chloro-7-(3-chloropropoxy)quinazoline 7-(3-Hydroxypropoxy)quinazolin-4(3H)-one, toluene and N,N-diisopropyl-formamide (DIPF) were mixed together and heated to 76° C., before thionyl chloride was added over a period of 1 hour at 76° C. Additional thionyl chloride was then added over a period of 1 hour after which the temperature was maintained at 76° C. for 1 hour. The mixture was refluxed for 11 hours to effect a clear solution which was cooled to 38° C. and subjected to vacuum distillation to remove toluene and thionyl chloride. Toluene was then added and the solution kept at 35° C. whilst it was clarified with a filter aid (celite or harborlite and activated carbon). The resulting solution was partially concentrated before heptane was added and the mixture chilled to 0° C. and stirred for 23 hours. The light brown suspension that formed was isolated by filtration, washed with cold heptane then dried in vacuo at 30° C. to yield 4-chloro-7-(3-chloropropoxy)quinazoline (63.6%)

$^1$H-NMR (DMSO $d_6$): 13.25 (br s, 1H), 8.34 (s, 1H), 8.06 (d, 1H), 7.17 (m, 2H), 4.21 (t, 2H), 3.83 (t, 2H), 2.23 (m, 2H):

MS (+ve ESI): 257, 259 (M+H)$^+$.

Preparation of (3-{[7-(3-chloropropoxy)quinazolin-4-yl]amino}-1H-pyrazol-5-yl)acetic acid 4-Chloro-7-(3-chloropropoxy)quinazoline was added to 1 molar equivalent of a solution of (3-amino-1H-pyrazol-5-yl) acetic acid in N-methylpyrrolidinone (NMP) and then left for a period of 12 hours. Crystallisation of the product was observed to occur with and without seeding and with and without the addition of acetonitrile as an anti-solvent. The resultant solid was isolated by filtration, washed with N-methylpyrrolidinone and acetonitrile and then dried in vacuo to yield (3-{[7-(3-chloropropoxy)quinazolin-4-yl]amino}-1H-pyrazol-5-yl)acetic acid.hydrochloride as an off-white solid containing one molar equivalent of NMP:

$^1$H-NMR (DMSO $d_6$): 8.92 (s, 1H), 8.79 (d, 1H), 7.45 (pr of d, 1H), 7.38 (d, 1H), 6.7 (s, 1H), 6.67 (s, 1H), 4.31 (t, 2H), 3.85 (t, 2H), 3.72 (s, 2H), 3.3 (t), 2.7 (s,), 2.27 (m, 2H), 2.18 (t), 1.9 (m):

MS (+ve ESI): 362.1015 (M+H)$^+$.

Preparation of 2-(3-{[7-(3-chloropropoxy)quinazolin-4-yl]amino}-1H-pyrazol-5-yl)-N-(3-fluorophenyl)acetamide To a suspension of (3-{[7-(3-chloropropoxy)quinazolin-4-yl]amino}-1H-pyrazol-5-yl)acetic acid.hydrochloride in N,N-dimethylacetamide (DMA) is added 4-dimethylaminopyridine (DMAP) whilst maintaining a temperature of 15-25° C. (ideally 15° C.) followed by N-methylmorpholine whilst also maintaining the temperature. 3-Fluoroaniline (in a large excess which ideally is between 10-15 mole equivalents) is added at such a rate as to maintain the temperature below 25° C. Meanwhile 1-ethyl-3-(3-dimethylaminopropyl) carbodiimide hydrochloride (EDCl.HCl) is dissolved in water to afford a solution about 42% w/v (the quantity of water present is important to the outcome of the crystallisation later in the process). This solution is added in a controlled manner to the slurry over a period of 8 hour so as to maintain the reaction between 20-25° C.; then the mixture is seeded with crystals of the preferred form of the product (ideally an amount of about 1% of the expected yield). The mixture is stirred for about 16 hours whilst maintaining the temperature (ideally 20-25° C.) then anti-solvents acetonitrile followed by water are added in a controlled manner and to maintain the temperature between 20-25° C. followed by an extended stir of about 21 hours; this is to optimise the recovery and form of the product. The material is isolated by filtration and the cake washed with a mixture of N,N-dimethylacetamide:water:acetonitrile (volume ratios of 5:3:2), acetonitrile and then dried (in vacuo or under a stream of nitrogen) to afford 2-(3-{[7-(3-chloropropoxy)quinazolin-4-yl]amino}-1H-pyrazol-5-yl)-N-(3-fluorophenyl)acetamide containing some DMA in about 76-78% yield.

$^1$H-NMR (DMSO $d_6$; contains residual DMA): 10.4 (s, 1H), 8.9 (s, 1H), 8.8 (d, 1H), 7.59 (pr of m, 1H), 7.46(pr of d, 1H), 7.33 (m, 2H), 7.29 (d, 1H), 6.85 (m, 1H), 6.75 (s, 1H), 4.35 (t, 2H), 3.85 (t, 4H), 2.95 (s), 2.83 (s), 2.56 (s), 2.25 (m, 2H), 1.95 (s):

MS (+ve): 455 (M+H)$^+$.

Preparation of 2-{3-[(7-[3-[ethyl(2-hydroxyethyl) amino]propoxy]-quinazolin-4-yl)amino]-1H-pyrazol-5-yl}-N-(3-fluorophenyl)acetamide (AZD1152 HOPA)

2-(3-{[7-(3-Chloropropoxy)quinazolin-4-yl]amino}-1H-pyrazol-5-yl)-N-(3-fluorophenyl)acetamide and 2-(ethylamino)ethanol (ideally 12 molar equivalents) were added to N,N-dimethylacetamide under an inert atmosphere (such as provided by nitrogen) and the mixture heated to 90° C. with stirring. After a period of 12-16 hours (ideally 12 hours) the reaction is cooled back to about 85° C. and water added in a controlled manner to maintain the temperature between 80-85° C. The batch is adjusted to 80° C. and seeded with crystals of the preferred form of the product (ideally an amount of about 1% of the expected yield). The mixture was cooled to 20° C. in a carefully controlled manner over a period of about 20 hours so as to crystallise the product in the required form and of a size sufficient to afford a good filtration rate. The product is then filtered and washed with a mixture of water/N,N-dimethylacetamide and acetonitrile and suitably deliquored to afford a hydrated form of the product. Following this, the cake is slurried in situ for a period (ideally 2 hours) with warm acetonitrile (ideally at a temperature of 40° C.) then filtered, washed with more acetonitrile and then dried (in vacuo or under a stream of nitrogen) to afford the almost anhydrous 2-{3-[(7-{3-[ethyl(2-hydroxyethyl)amino]propoxy}-quinazolin-4-yl)amino]-1H-pyrazol-5-yl}-N-(3-fluorophenyl)acetamide as an off-white solid in a yield of 85-90%.

$^1$H-NMR (DMSO $d_6$): 10.55 (s, 1H), 9.45 (br s, 1H), 8.98 (s, 1H), 8.8 (d, 1H), 7.63 (pr of m, 1H), 7.47 (pr of d, 1H), 7.37 (m, 2H), 7.32 (d, 1H), 6.9 (m, 1H), 6.77 (s, 1H), 4.32 (t, 2H), 3.83 (br s, 2H), 3.76 (t, 2H), 3.35 (m, 2H), 3.25 (m, 4H), 2.25 (m, 2H), 1.25 (t, 3H):

MS (+ve ESI): 508.4 (M+H)$^+$.

Preparation of mono(tert-butyl) 2-[[3-([4-[(5-[2-[(3-fluorophenyl)amino]-2-oxoethyl]-1H-pyrazol-3-yl) amino]-quinazolin-7-yl]oxy)propyl](ethyl)amino] ethyl phosphate [AZD1152 t-Bu P(5)ester]

2-{3-[(7-{3-[Ethyl(2-hydroxyethyl)amino]propoxy}-quinazolin-4-yl)amino]-1H-pyrazol-5-yl}-N-(3-fluorophenyl)acetamide and pyridine.hydrochloride were mixed in N,N-dimethylacetamide and the solution chilled to −15° C. Di-tert-butyl diethylphosphoramidite (1.5-2.1 molar equivalents) was then added whilst the temperature was maintained. The reaction mixture was treated in situ with 30% w/w hydrogen peroxide (about 4.2 mole equivalents) whilst the temperature was kept below ambient temperature. Remaining hydrogen peroxide was destroyed by the addition of sodium metabisulphite (as a 10% w/v solution) whilst maintaining the temperature below 40° C. The resulting solution of di-tert-butyl 2-[[3-({4-[(5-{2-[(3-fluorophenyl)amino]-2-oxoethyl}-1H-pyrazol-3-yl)amino]quinazolin-7-yl}oxy)propyl](ethyl)amino]ethyl phosphate was then heated to 40° C. and sodium hydroxide solution (2M) added to adjust to pH 5-6.5.

The temperature and pH was maintained for a period of about 90 minutes with seeding. Water was then charged and the pH adjusted further to within the range pH 8-9 to optimise the recovery. The warm reaction mixture was filtered directly to afford mono-tert-butyl 2-[[3-({4-[(5-{2-[(3-fluorophenyl)amino]-2-oxoethyl}-1H-pyrazol-3-yl)amino]quinazolin-7-yl}oxy)propyl](ethyl)amino]ethyl phosphate which washed with a mixture of N,N-dimethylacetamide/water and water and finally dried (in vacuo or a stream of a suitable inert gas) to afford mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate as an off-white solid at a yield of between 86-93%.

$^1$H-NMR (DMSO $d_6$): 10.48 (s, 1H), 9.75 (br s, 1H), 8.98 (s, 1H), 8.85 (d, 1H), 7.67 (pr of m, 1H), 7.48(pr of d, 1H), 7.37 (m, 2H), 7.3 (d, 1H), 6.87 (m, 1H), 6.83 (s, 1H), 4.34 (t, 2H), 4.28 (m, 2H), 3.88 (s, 2H), 3.53 (m, 2H), 3.43 (m, 2H), 3.33 (m, 2H), 2.3 (m, 2H), 1.47 (s, 9H), 1.32 (t, 3H):

MS (+ve ESI): (M+H)$^+$ 644.2761 fragment (less butyl) 588.2147

Preparation of mono(tert-butyl) 2-[[3-([4-[(5-[2-[(3-fluorophenyl)amino]-2-oxoethyl]-1H-pyrazol-3-yl)amino]-quinazolin-7-yl]oxy)propyl](ethyl)amino]ethyl phosphate [AZD1152 t-Bu P(5)ester]—Alternative Route To a slurry of pyridine.hydrochloride in N,N-dimethylacetamide was charged a solution of 2-{3-[(7-{3-[Ethyl(2-hydroxyethyl)amino]propoxy}-quinazolin-4-yl)amino]-1H-pyrazol-5-yl}-N-(3-fluorophenyl)acetamide and di-tert-butyl diethylphosphoramidite (ideally 1 molar equivalents) in N,N-dimethylacetamide over an extended period (ideally 3 hours) and maintaining the temperature between −20 to −10° C. (ideally −15° C.). This is followed by the further addition of di-tert-butyl diethylphosphoramidite (ideally 0.5 molar equivalents) during a period of 1 hour also maintaining the temperature between −20 to −10° C. (ideally −15° C.).

The reaction mixture is treated in situ with 30% w/w hydrogen peroxide (about 4.2 mole equivalents) whilst the temperature was kept below −10° C. (ideally −12 to −8° C.) and held for a period at this temperature (ideally 16 hours). Remaining hydrogen peroxide is destroyed by the addition of sodium metabisulphite (as a 10% w/v aqueous solution) whilst maintaining the temperature below 40° C.

The resulting solution of di-tert-butyl 2-[[3-({4-[(5-{2-[(3-fluorophenyl)amino]-2-oxoethyl}-1H-pyrazol-3-yl)amino]quinazolin-7-yl}oxy)propyl](ethyl)amino]ethyl phosphate was then heated to 40° C. and sodium hydroxide solution (ideally 2M) added to adjust to pH 5.5-6.5 (ideally pH 6) with seeding with suitably crystalline material. The temperature is held and a range of pH 5-6 maintained by the addition of extra sodium hydroxide solution for a period of at least 2 hours. Water is then charged and the pH adjusted further to within the range pH 8-9 (ideally pH 8.8) whilst maintaining the temperature (ideally 40° C. but within range 35-45° C.) for a period of 16 hours so as to optimise the recovery. The warm reaction mixture is filtered directly to afford mono-tert-butyl 2-[[3-({4-[(5-{2-[(3-fluorophenyl)amino]-2-oxoethyl}-1H-pyrazol-3-yl)amino]quinazolin-7-yl}oxy)propyl](ethyl)amino]ethyl phosphate which washed several times with water and finally dried (either in vacuo or a stream of a suitable inert gas) to afford the mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate as an off-white solid at a yield of between 86-93%.

$^1$H-NMR (DMSO $d_6$): 10.48 (s, 1H), 9.75 (br s, 1H), 8.98 (s, 1H), 8.85 (d, 1H), 7.67 (pr of m, 1H), 7.48(pr of d, 1H), 7.37 (m, 2H), 7.3 (d, 1H), 6.87 (m, 1H), 6.83 (s, 1H), 4.34 (t, 2H), 4.28 (m, 2H), 3.88 (s, 2H), 3.53 (m, 2H), 3.43 (m, 2H), 3.33 (m, 2H), 2.3 (m, 2H), 1.47 (s, 9H), 1.32 (t, 3H):

MS (+ve ESI): (M+H)$^+$ 644.2761 fragment (less butyl) 588.2147.

Preparation of 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate (AZD1152)

Mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate was suspended in a mixture of water/tetrahydrofuran (THF) and treated with an excess of between 1.5 and 3.0 molar equivalents of hydrochloric acid (ideally of a concentration of 2M and containing 1.5 mole equivalents). The mixture is heated to 55-65° C. (ideally 60° C.) and held at 60° C. for about 1 hour. The hot solution is then basified using sodium hydroxide (preferably of 2M concentration and containing 1.7 mole equivalents) to afford a pH within the range pH 5.0-5.5 and then seeded at 55-65° C. (ideally 60° C.) with crystals of the preferred form of the product (ideally an amount of about 0.05% w/w of the expected yield). The mixture is stirred at this temperature for at least one hour before water is added and the slurry stirred and cooled in a controlled manner over a period of about 12 hours prior to stirring at ambient temperature for at least 4 hours and then isolating the product by filtration. The filtercake is washed successively with water then THF and dried either in vacuo or using a humidification procedure whereby an inert gas dampened with water vapour is passed over the solid until a constant weight is obtained. After the drying in vacuo the solid 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate is equilibrated under ambient conditions to constant weight to give a hydrated form as a pale yellow needle-like material. The product is obtained in about 81% yield.

$^1$H-NMR (DMSO $d_6$):
MS (+ve ESI): 587.8 (M+H)$^+$
$^1$H-NMR (DMSO $d_6$): 10.53 (s, 1H), 8.57 (s, 1H), 8.54 (d, 1H), 7.62 (d, 1H), 7.37 (m, 2H), 7.27 (s, 1H), 7.21 (d, 1H), 6.88 (m, 1H), 6.65 (s, 1H), 4.27 (t, 2H), 4.05 (m, 2H), 3.75 (s, 2H), 3.24 (m, 2H), 3.21 (t, 2H), 3.13 (q, 2H), 2.18 (m, 2H), 1.24 (t, 3H)
MS (+ve ESI): 588 (M+H)$^+$.
$C_{26}H_{31}FN_7O_6P+3.0H_2O$ requires C, 48.7%; H, 5.8%; N, 15.3%; Found C, 48.8%; H, 5.35%; N, 15.15%.

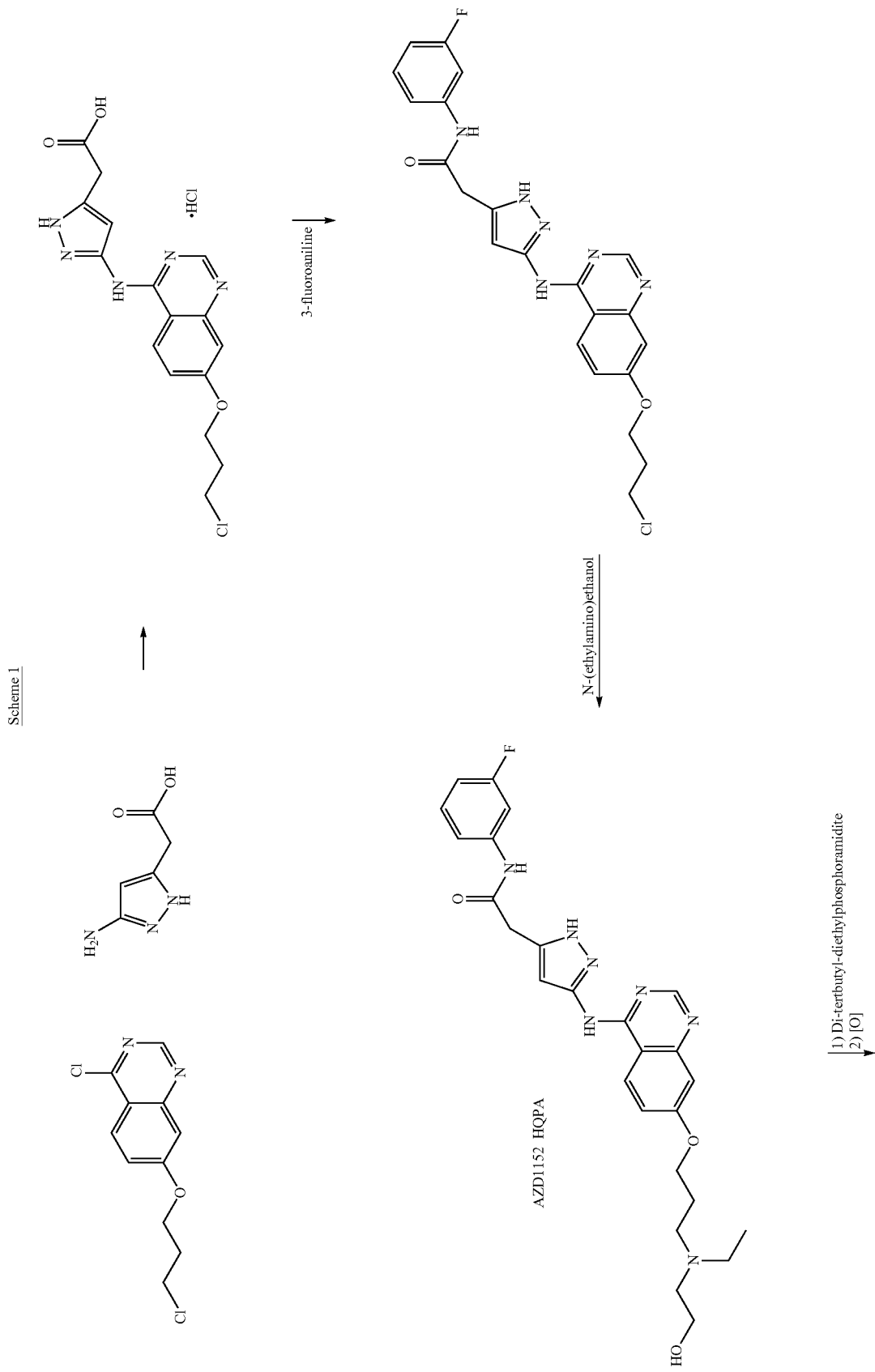
Scheme 1

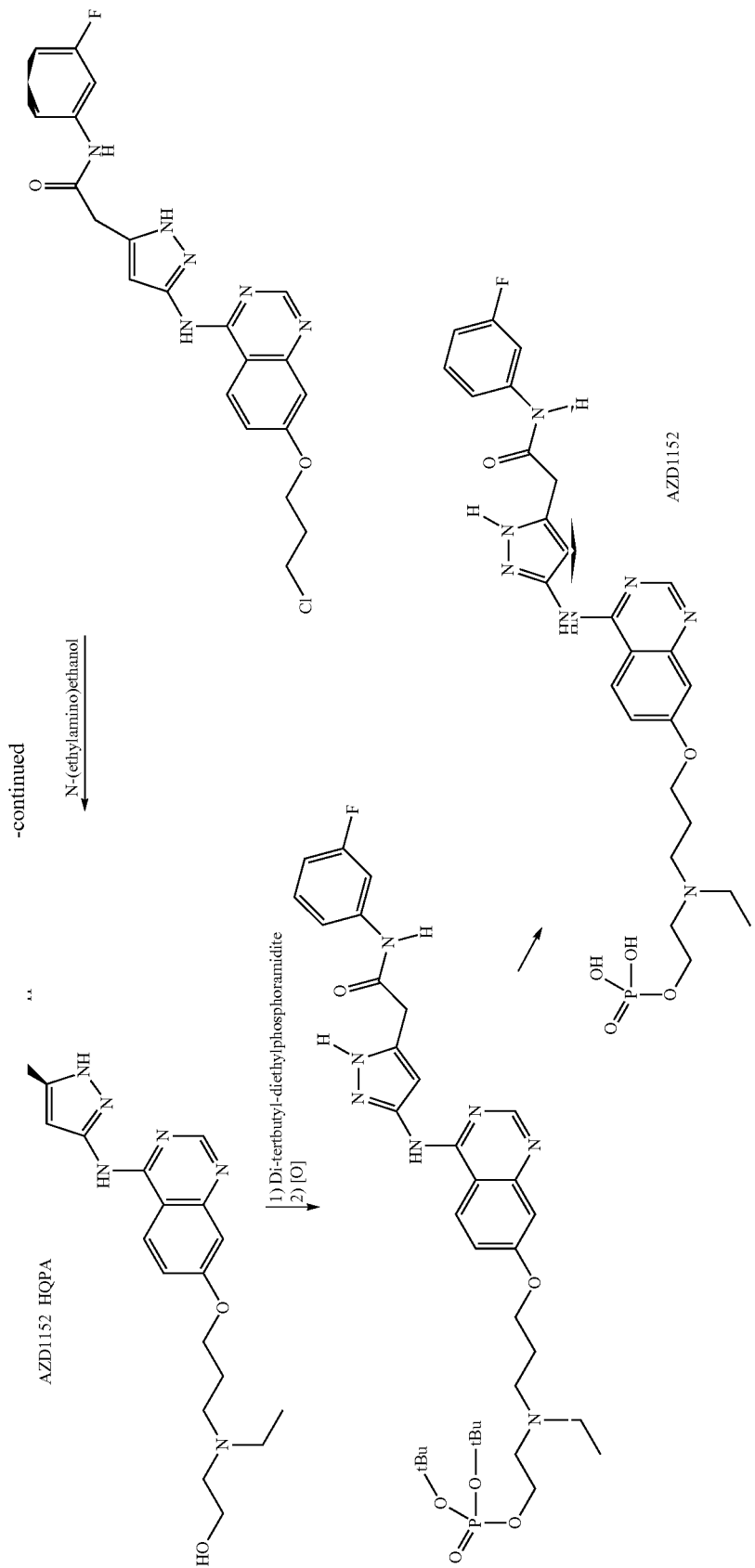

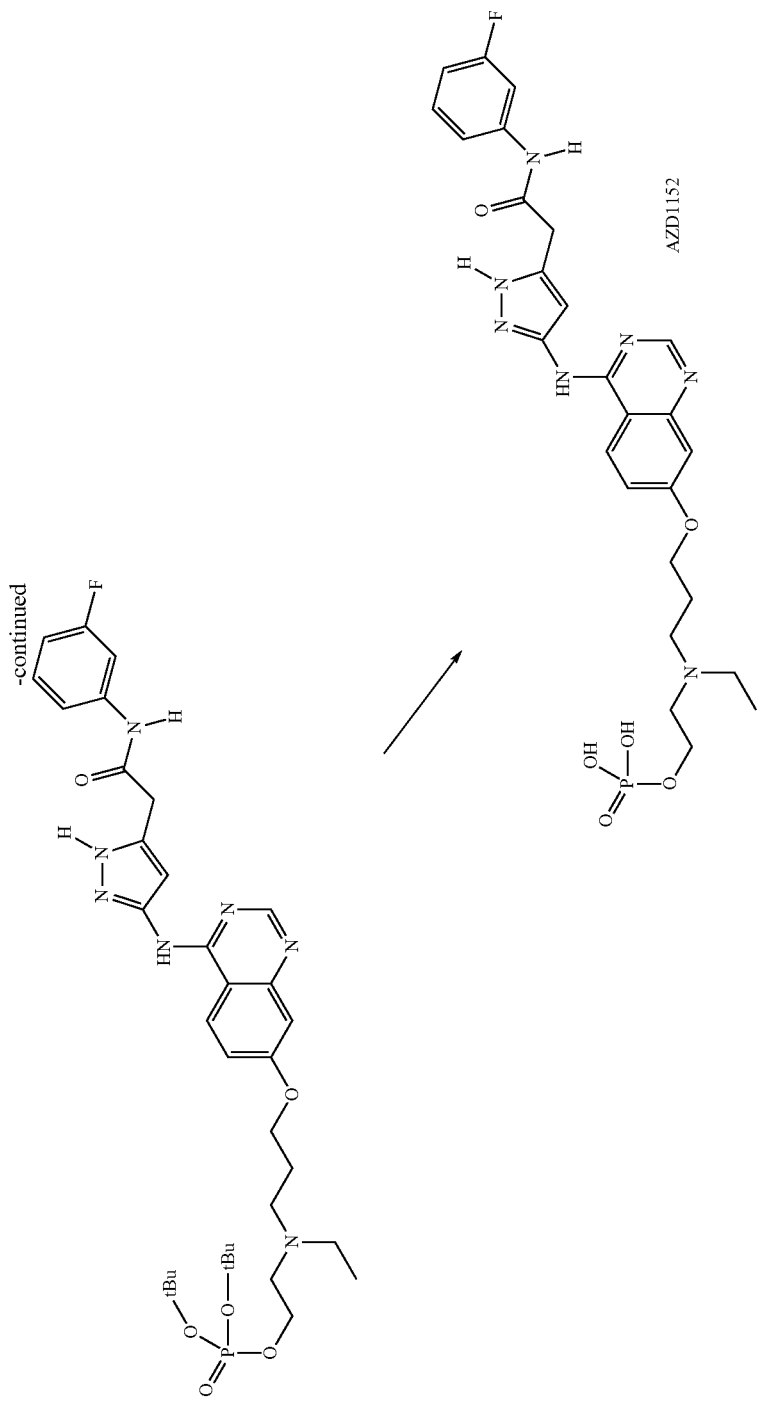

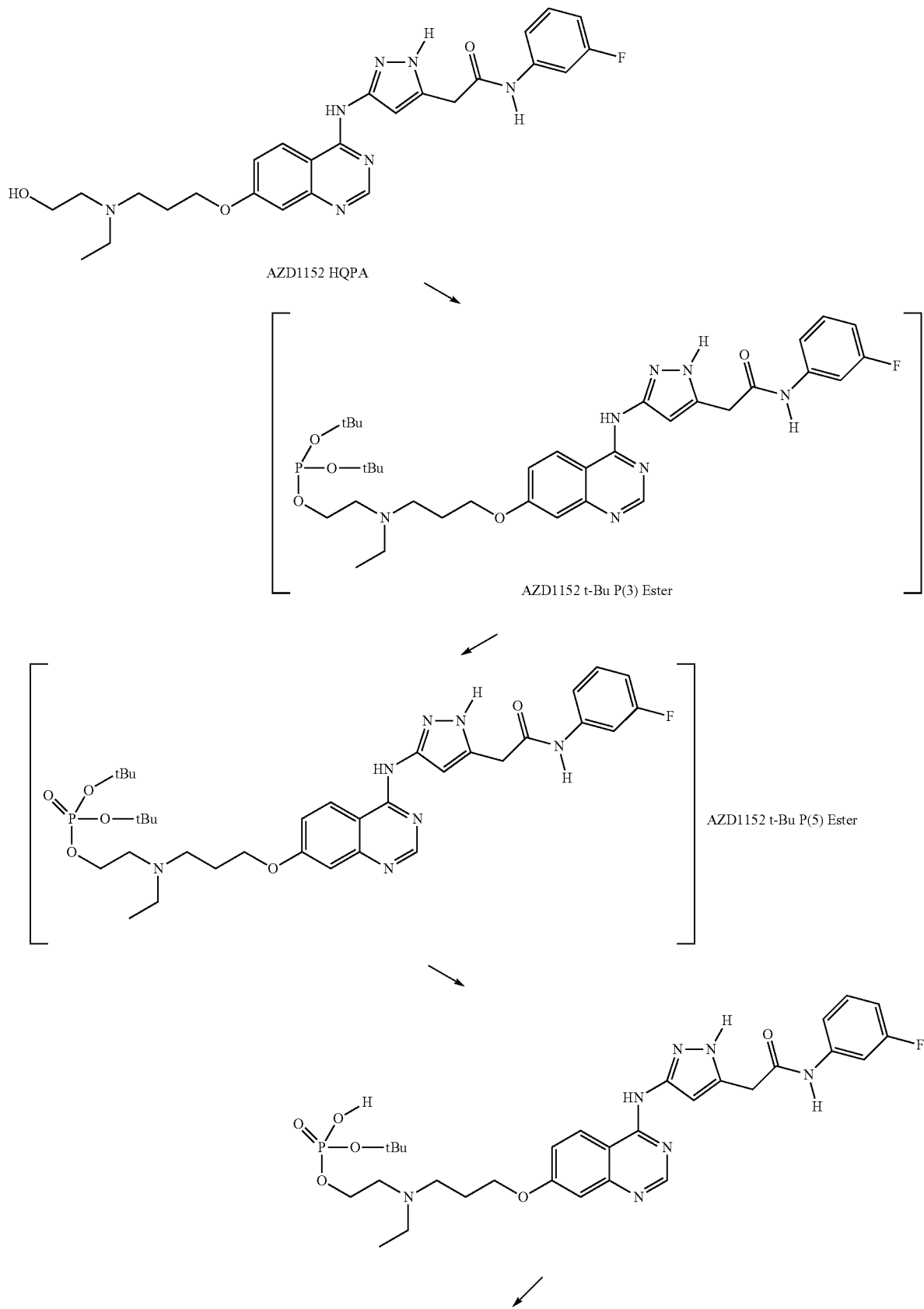

-continued

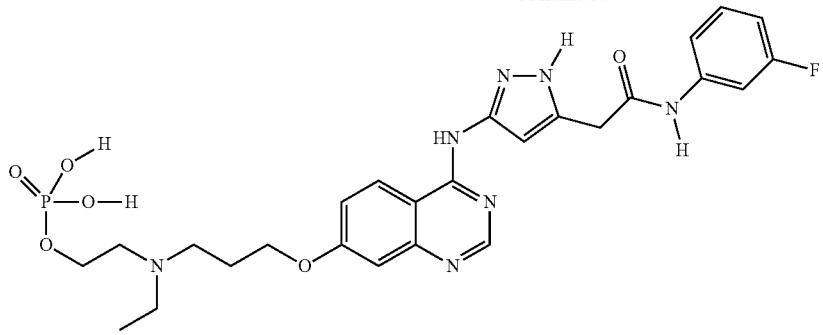

AZD1152

The invention claimed is:

1. A process for preparing an intermediate compound of formula (IIA)

formula (IIA)

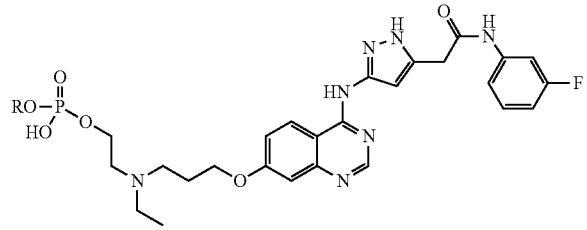

wherein R is an acid labile protecting group selected from tert-butyl, trityl, p-methoxyphenyl, benzyl or phenyl;

which process comprises adjusting the pH of a solution of a compound of formula (IIIA)

formula (IIIA)

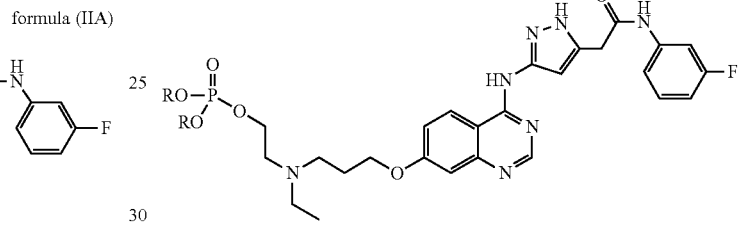

wherein R is as defined in relation to formula (IIA); to pH 5 to 6.5 at a temperature of −10° C. to ambient temperature.

2. A process for the preparation of AZD 1152 (formula (IA))

formula (IA)

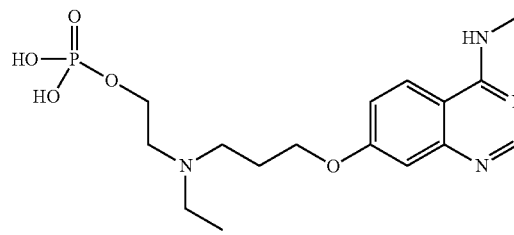

from a compound of formula (IIA)

formula (IIA)

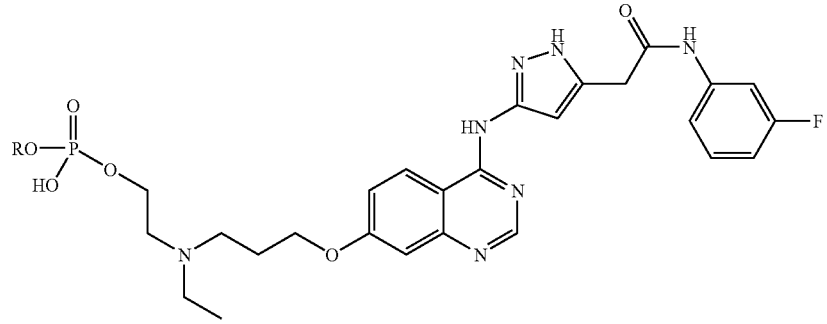

wherein R is tert-butyl;
which process comprises the steps of:
1) adding a suitable acid to a solution of a compound of formula (IA); and
2) adjusting the pH of the resulting mixture to pH 4.5 to 5.5.

3. A process for the preparation of AZD1152 (formula (IA))

formula (IA)

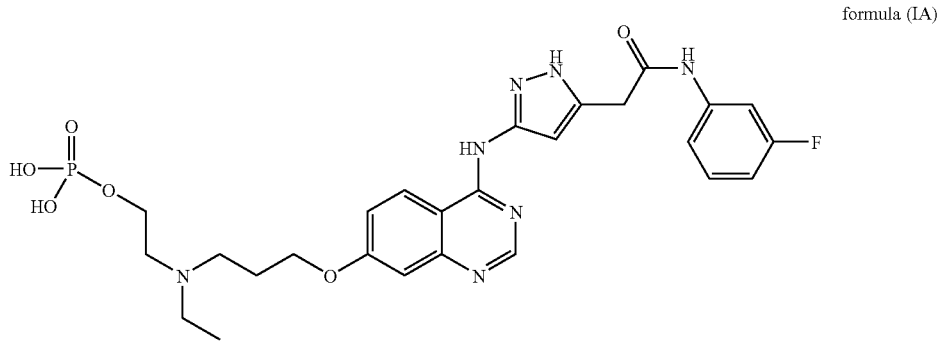

from a compound of formula (IIIA)

formula (IIIA)

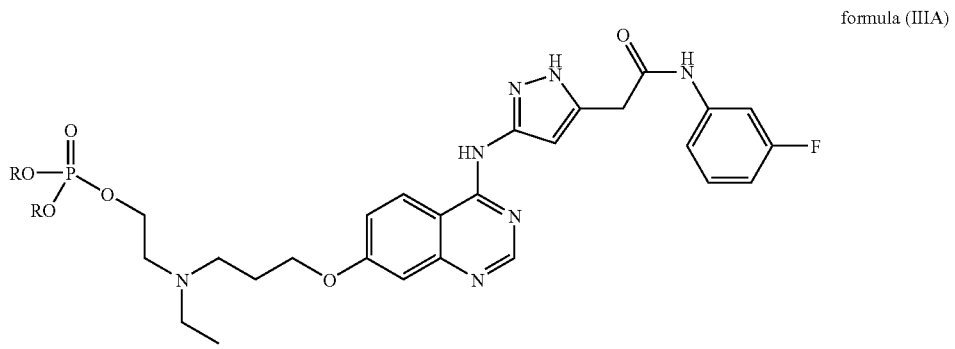

wherein the process comprises the steps of:
(i) adjusting the pH of a solution of a compound of formula (IIIA), wherein R is tert-butyl, to pH 5 to 6.5 at a temperature of −10° C. to ambient temperature to form a compound of Formula (IIA):

formula (IIA)

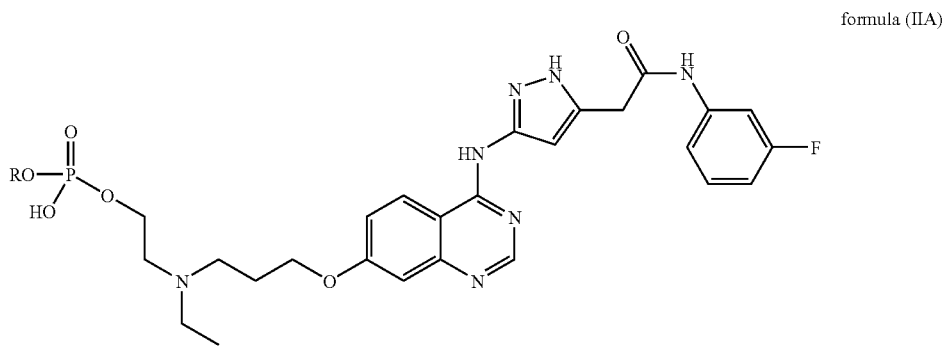

(ii) adding a suitable acid to a solution of compound of formula (IIA); and
(iii) adjusting the pH of the resulting mixture to pH 4.5 to 5.5 to form AZD1152 (formula (IA)).

4. A compound of formula (IIA)

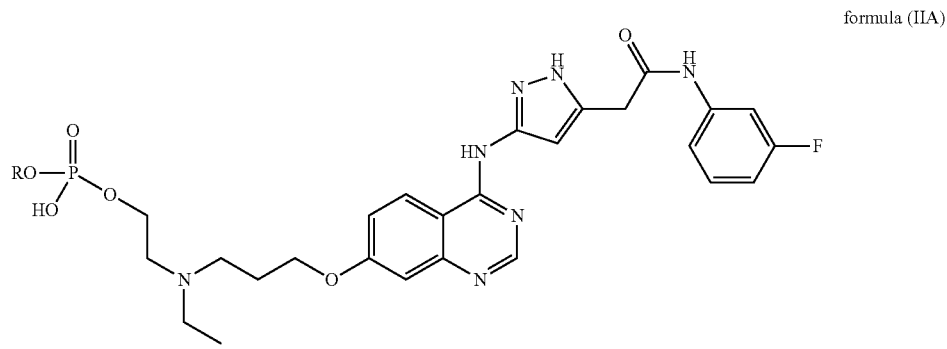

formula (IIA)

wherein R is an acid labile protecting group selected from tert-butyl, trityl, p-ethoxyphenyl, benzyl or phenyl.

5. A process for the preparation of a pharmaceutically acceptable salt of AZD 1152 (formula (IA))

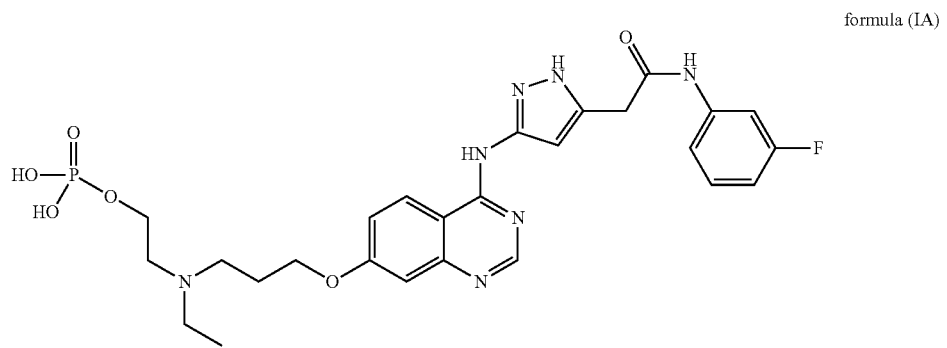

formula (IA)

from a compound of formula (IIA)

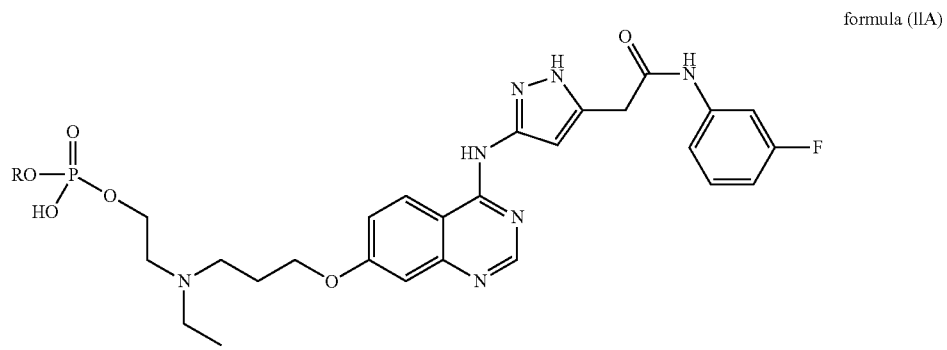

formula (IIA)

wherein R is tert-butyl;

which process comprises the steps of:

1) adding a suitable acid to a solution of a compound of formula (IA);
2) adjusting the pH of the resulting mixture to pH 4.5 to 5.5; and
3) forming a pharmaceutically acceptable salt of AZD1152.

6. A process for the preparation of a pharmaceutically acceptable salt of AZD1152 (formula (IA))

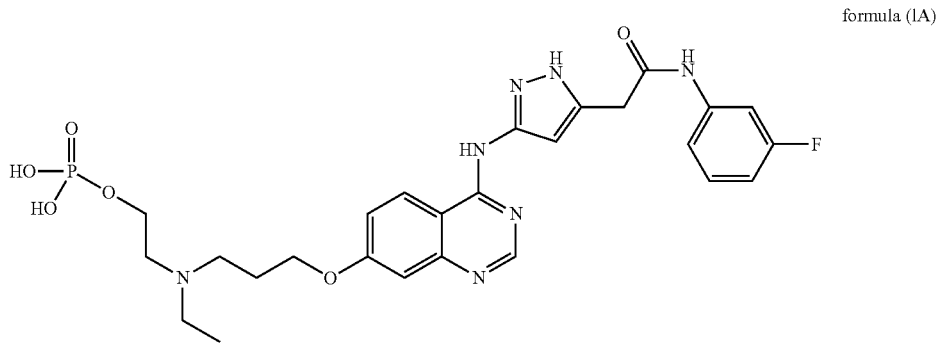

formula (IA)

from a compound of formula (IIIA)

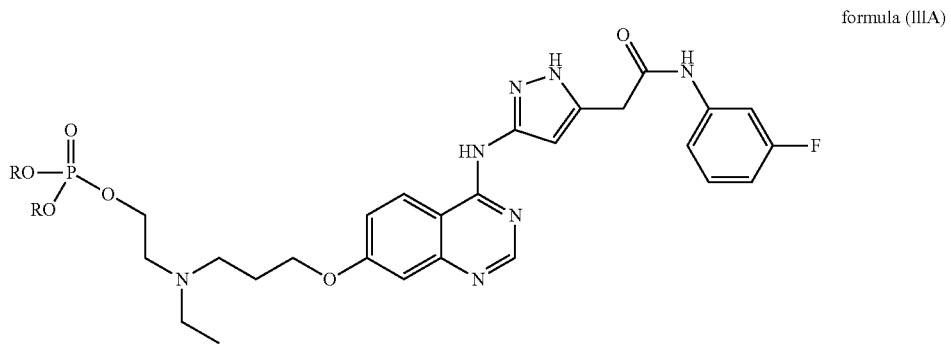

formula (IIIA)

wherein the process comprises the steps of:
(i) adjusting the pH of a solution of a compound of formula (IIIA), wherein R is tert-butyl, to pH 5 to 6.5 at a temperature of −10° C. to ambient temperature to form a compound of Formula (IIA):

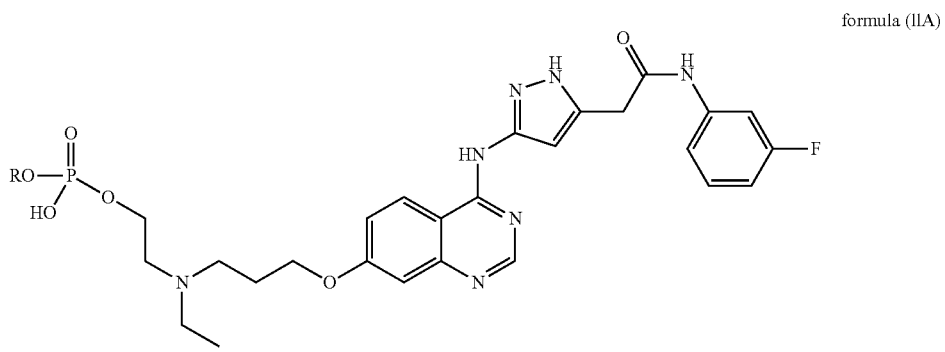

formula (IIA)

(ii) adding a suitable acid to a solution of a compound of formula (IIA);
(iii) adjusting the pH of the resulting mixture to pH 4.5 to 5.5 to form AZD1152 (formula (IA)); and (iii) forming a pharmaceutically acceptable salt of AZD 1152.

* * * * *